(12) United States Patent
Gingles

(10) Patent No.: US 7,922,687 B2
(45) Date of Patent: Apr. 12, 2011

(54) CATHETER WITH CENTERING WIRE

(75) Inventor: Bruce Gingles, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1339 days.

(21) Appl. No.: 10/991,289

(22) Filed: Nov. 16, 2004

(65) Prior Publication Data
US 2005/0148929 A1   Jul. 7, 2005

Related U.S. Application Data

(60) Provisional application No. 60/520,601, filed on Nov. 17, 2003.

(51) Int. Cl.
*A61M 3/00* (2006.01)

(52) U.S. Cl. .......... 604/43; 604/4.01; 604/5.01; 604/29; 604/271

(58) Field of Classification Search .............. 604/43, 604/4.01, 29, 164.13, 271, 5.01, 510, 106, 604/107

See application file for complete search history.

(56) References Cited

U.S. PATENT DOCUMENTS

| | | |
|---|---|---|
| 3,938,530 A | 2/1976 | Santomieri |
| 3,946,741 A | 3/1976 | Adair |
| 4,129,129 A | 12/1978 | Amrine |
| 4,134,402 A | 1/1979 | Mahurkar |
| 4,154,242 A | 5/1979 | Termanini |
| 4,493,696 A | 1/1985 | Uldall |
| RE31,855 E | 3/1985 | Osborne |
| 4,581,025 A | 4/1986 | Timmermans |
| 4,643,711 A | 2/1987 | Bates |
| 4,655,745 A | 4/1987 | Corbett |
| 4,680,029 A | 7/1987 | Ranford et al. |
| 4,733,669 A | 3/1988 | Segal |
| 4,772,268 A | 9/1988 | Bates |
| 4,808,163 A | 2/1989 | Laub |
| 4,878,893 A | 11/1989 | Chin |
| 4,904,238 A | 2/1990 | Williams |
| 4,973,301 A | 11/1990 | Nissenkorn |
| 4,995,868 A | 2/1991 | Brazier |
| 5,106,368 A | 4/1992 | Uldall et al. |
| 5,156,597 A | 10/1992 | Verreet et al. |
| 5,193,533 A | 3/1993 | Body et al. |
| 5,221,256 A | 6/1993 | Mahurkar |
| 5,275,610 A | 1/1994 | Eberbach |

(Continued)

FOREIGN PATENT DOCUMENTS

EP   0 301 854 A2   2/1989

(Continued)

*Primary Examiner* — Nicholas D Lucchesi
*Assistant Examiner* — Quynh-Nhu H Vu
(74) *Attorney, Agent, or Firm* — Brinks Hofer Gilson & Lione

(57) ABSTRACT

A catheter assembly for use in the extracorporeal treatment of bodily fluids. The assembly comprises a catheter body having a withdrawal port, an infusion port, and a plurality of lumens therein. One of the lumens comprises a withdrawal lumen for transport of fluids withdrawn from a body vessel through the withdrawal port to an extracorporeal treatment unit, such as a dialyzer. Another lumen comprises an infusion lumen for return of treated fluids from the extracorporeal treatment unit into the body vessel through the infusion port. A wire extends from yet another lumen to an attachment point on the catheter assembly. The wire is capable of bowing radially outwardly from the catheter body, in order to space the infusion and withdrawal ports from the vessel wall.

16 Claims, 7 Drawing Sheets

U.S. PATENT DOCUMENTS

| | | |
|---|---|---|
| 5,352,198 A | 10/1994 | Goldenberg et al. |
| 5,409,460 A | 4/1995 | Krumme |
| 5,443,449 A | 8/1995 | Buelna |
| 5,486,159 A | 1/1996 | Mahurkar |
| 5,509,897 A | 4/1996 | Twardowski et al. |
| 5,514,112 A | 5/1996 | Chu et al. |
| 5,518,498 A | 5/1996 | Lindenberg et al. |
| 5,522,400 A | 6/1996 | Williams |
| 5,549,245 A * | 8/1996 | Kish ............................ 238/283 |
| 5,571,093 A | 11/1996 | Cruz et al. |
| 5,681,280 A | 10/1997 | Rusk et al. |
| 5,702,365 A | 12/1997 | King |
| 5,713,853 A | 2/1998 | Clark et al. |
| 5,749,826 A | 5/1998 | Faulkner |
| 5,817,067 A | 10/1998 | Tsukada |
| 5,857,464 A | 1/1999 | Desai |
| 5,885,258 A | 3/1999 | Sachdeva et al. |
| 5,888,196 A | 3/1999 | Bonutti |
| 5,957,900 A | 9/1999 | Ouchi |
| 6,001,079 A | 12/1999 | Pourchez |
| 6,033,397 A | 3/2000 | Laufer et al. |
| 6,052,612 A | 4/2000 | Desai |
| 6,071,263 A | 6/2000 | Kirkman |
| 6,177,049 B1 | 1/2001 | Schnell et al. |
| 6,238,412 B1 | 5/2001 | Dubrul et al. |
| 6,270,490 B1 | 8/2001 | Hahnen |
| 6,283,940 B1 | 9/2001 | Mulholland |
| 6,336,933 B1 | 1/2002 | Parodi |
| 6,409,700 B1 | 6/2002 | Siegel, Jr. et al. |
| 6,461,321 B1 | 10/2002 | Quinn |
| 6,475,207 B1 | 11/2002 | Maginot et al. |
| 6,517,529 B1 | 2/2003 | Quinn |
| 6,527,737 B2 | 3/2003 | Kaneshige |
| 6,547,761 B2 | 4/2003 | Liu |
| 6,558,349 B1 * | 5/2003 | Kirkman ........................ 604/104 |
| 6,558,350 B1 | 5/2003 | Hart et al. |
| 6,569,150 B2 | 5/2003 | Teague et al. |
| 6,579,302 B2 | 6/2003 | Duerig et al. |
| 2001/0011182 A1 | 8/2001 | Dubrul et al. |
| 2001/0018576 A1 | 8/2001 | Quinn |
| 2002/0026156 A1 | 2/2002 | Quinn |
| 2002/0072768 A1 | 6/2002 | Ginn |
| 2002/0143292 A1 | 10/2002 | Flinchbaugh |
| 2002/0177822 A1 | 11/2002 | St. Cyr et al. |
| 2003/0032918 A1 | 2/2003 | Quinn |
| 2003/0139763 A1 | 7/2003 | Duerig et al. |
| 2005/0177094 A1 * | 8/2005 | Igarashi et al. .................. 604/43 |

FOREIGN PATENT DOCUMENTS

| | | |
|---|---|---|
| WO | WO 01/19425 A1 | 3/2001 |
| WO | WO 02/064202 A3 | 8/2002 |

* cited by examiner

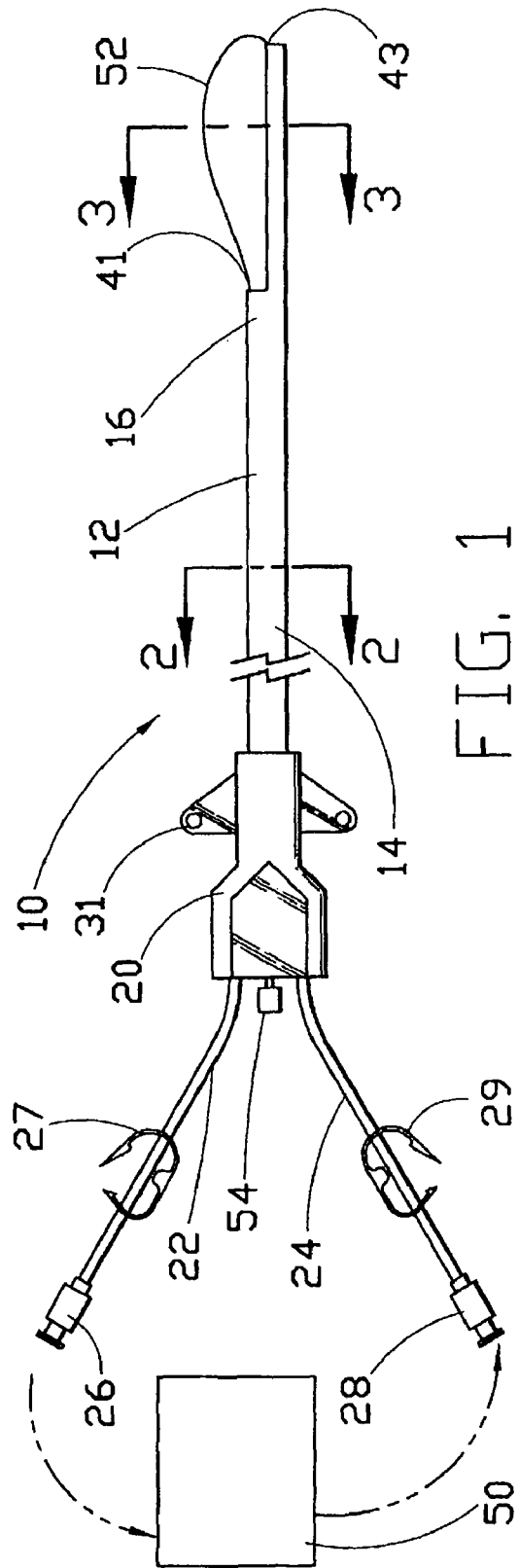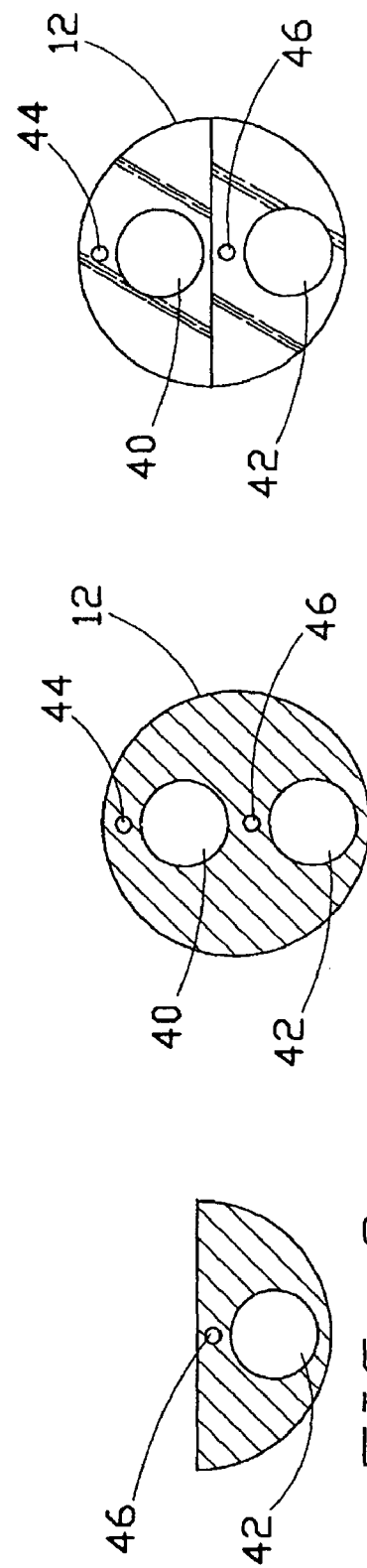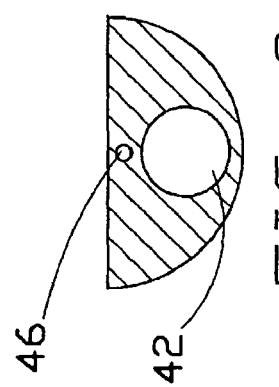

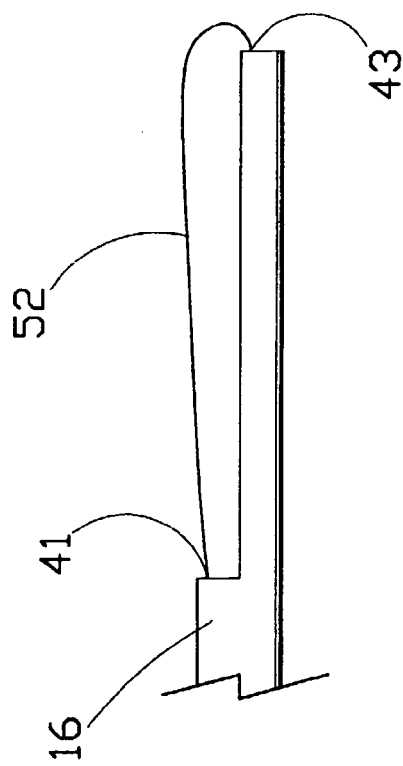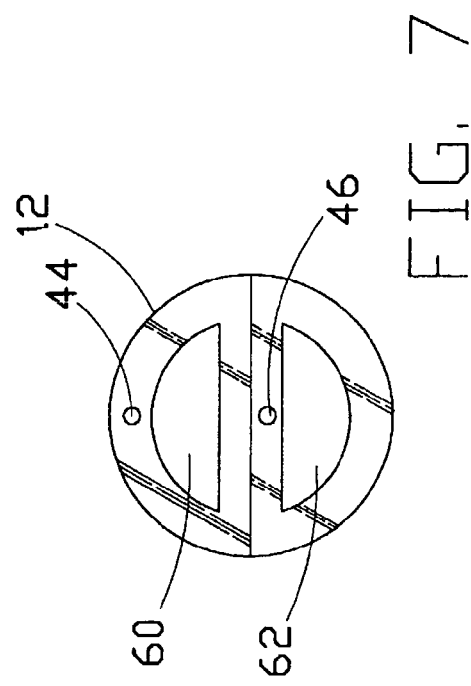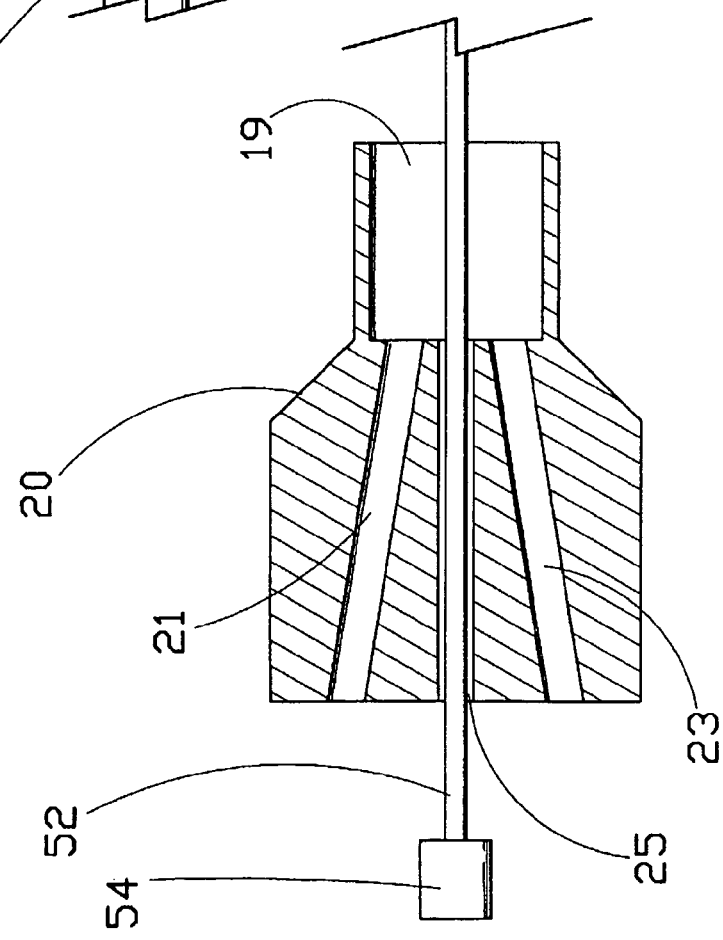

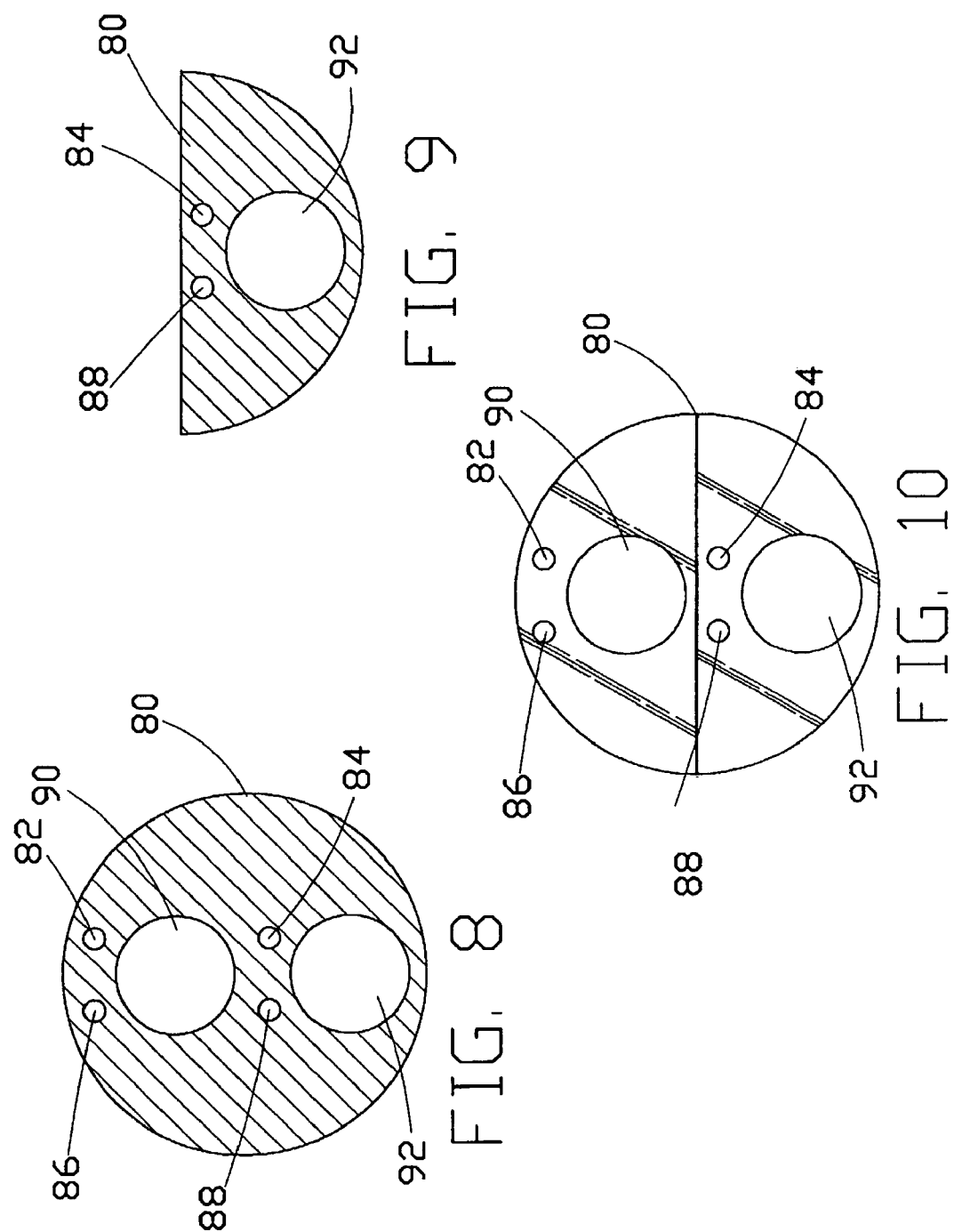

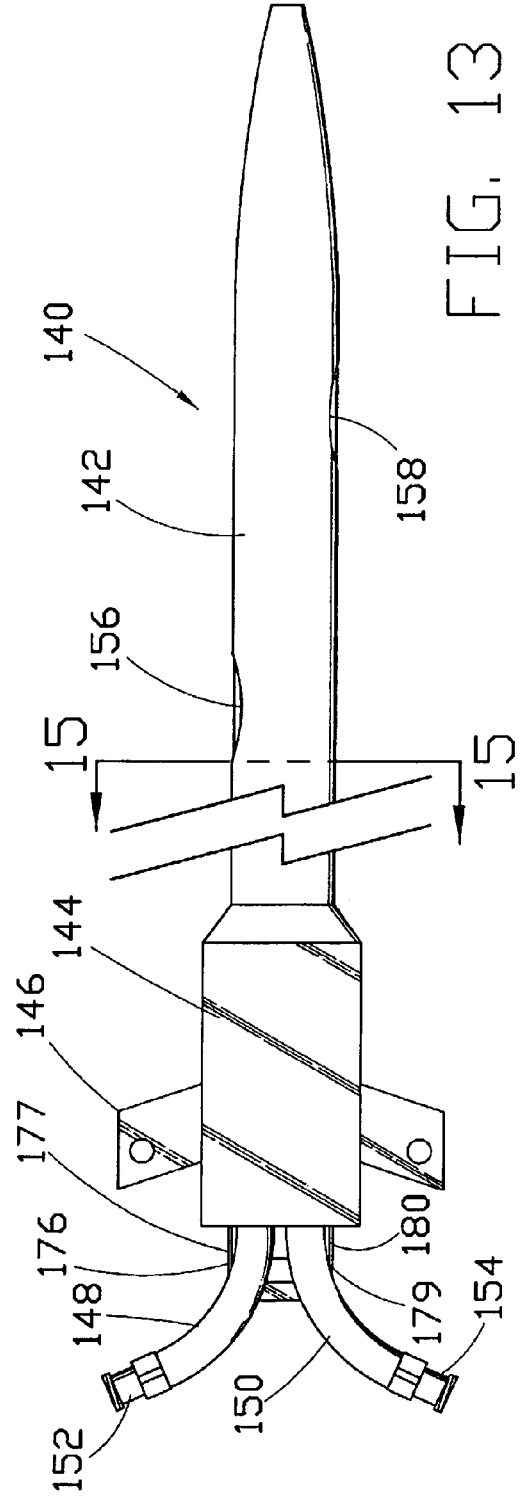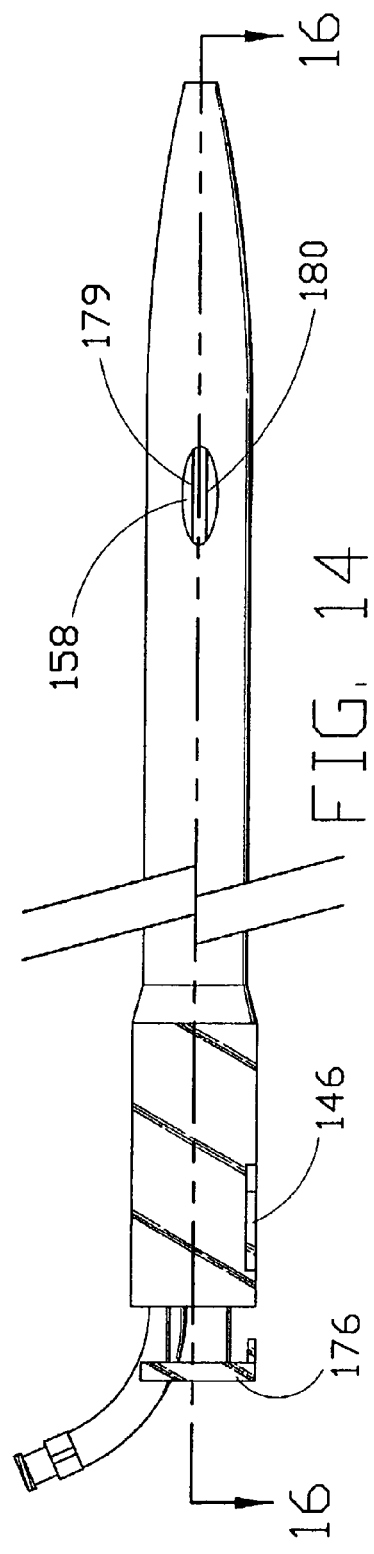

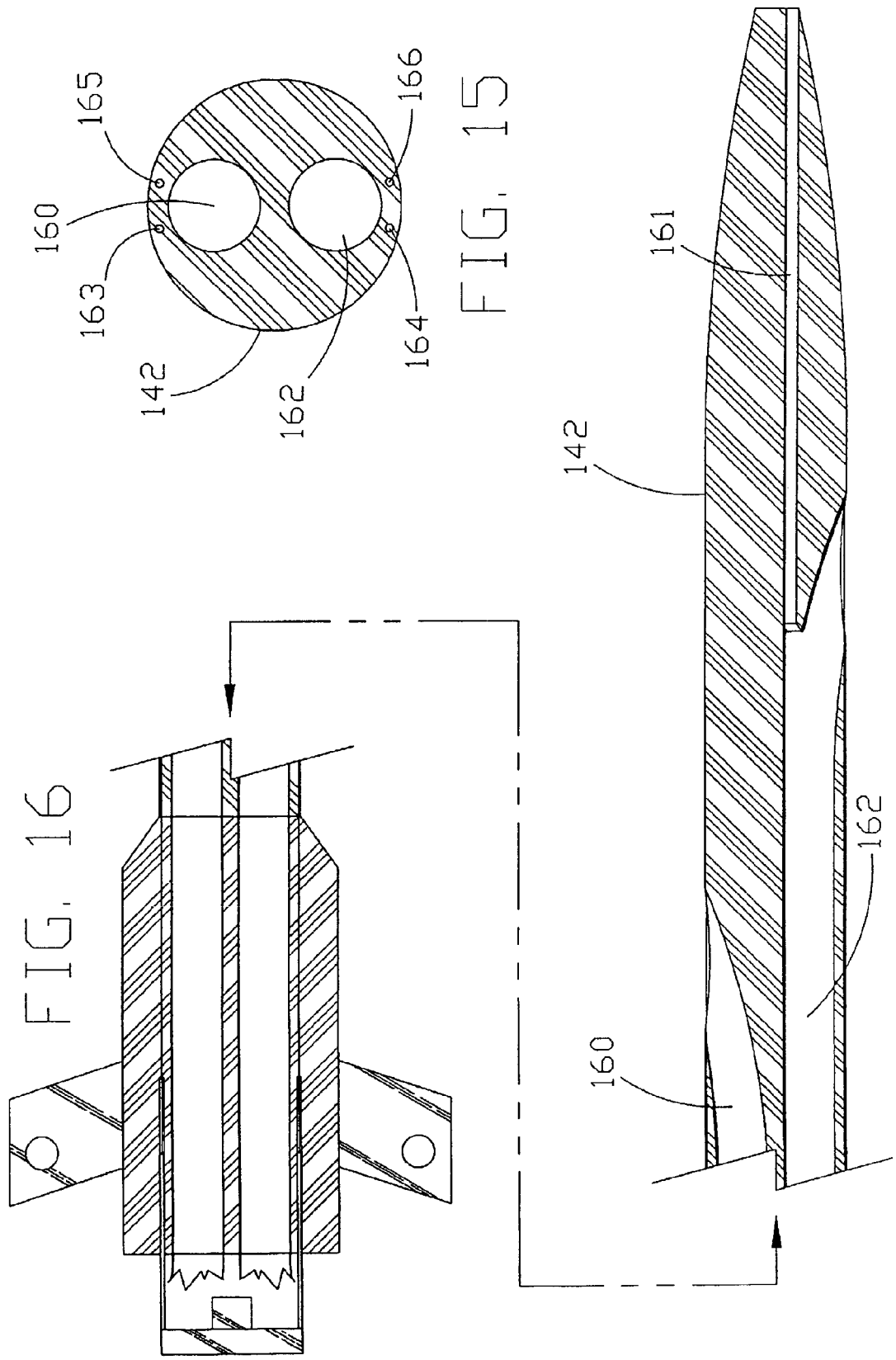

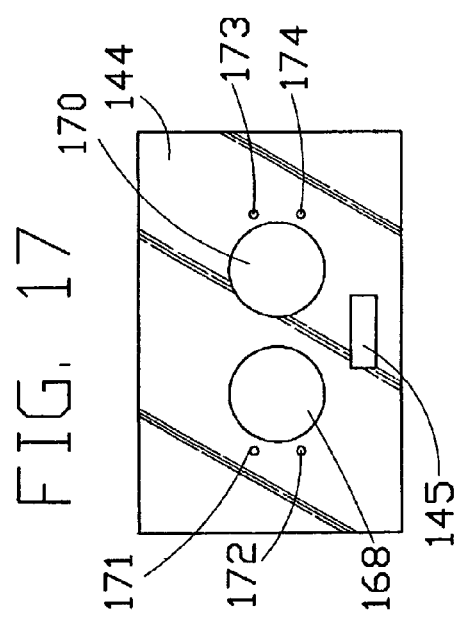
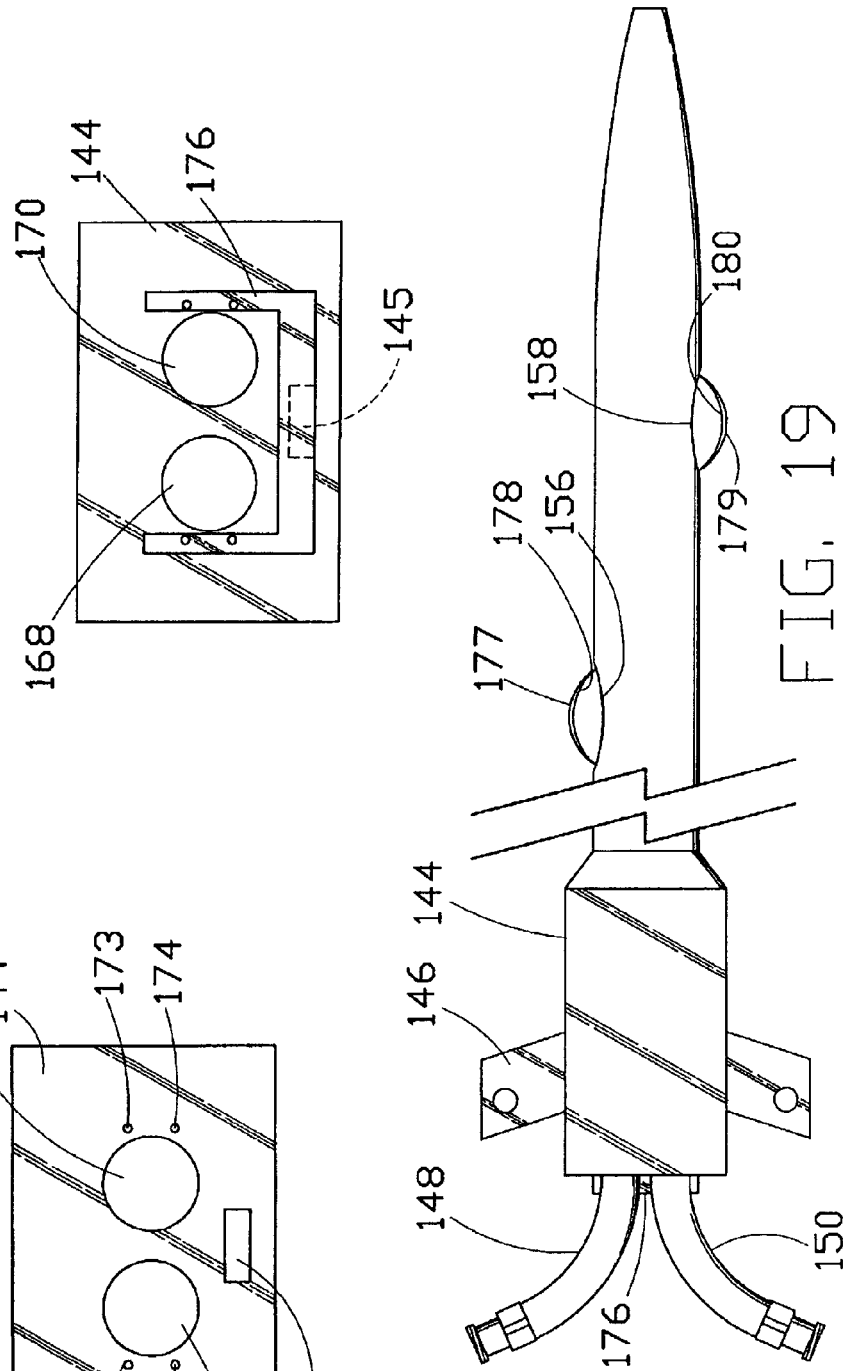

CATHETER WITH CENTERING WIRE

RELATED APPLICATIONS

The present patent document claims the benefit of the filing date under 35 U.S.C. §119(e) of Provisional U.S. Patent Application Ser. No. 60/520,601, filed Nov. 17, 2003, which is hereby incorporated by reference.

BACKGROUND

The present application relates generally to a catheter for use in transporting fluids, and particularly, to a catheter for transporting bodily fluids for extracorporeal treatment, and returning the treated fluids to the body.

Dual lumen catheters are commonly used for transporting bodily fluids for extracorporeal treatment. A fluid is withdrawn from the body through one of the lumens, generally referred to as the withdrawal lumen. The fluid is subjected to a treatment process, and thereafter returned to the body through the other lumen, generally referred to as the infusion lumen.

In many cases, the extracorporeal treatment involves a hemodialysis procedure. During hemodialysis, blood is withdrawn from a blood vessel through the withdrawal lumen and routed to a dialyzer for treatment. The cleansed blood is then returned to the vessel through the infusion lumen. When such a catheter is used for hemodialysis, it is generally inserted into the body through either the jugular vein, subclavian vein or femoral vein. In addition to hemodialysis, extracorporeal catheters can also be used for other procedures in which a fluid is removed from the body for treatment and later returned to the body. Two such examples are pheresis and hemofiltration.

A variety of hemodialysis catheters are commercially available. Among the types of commercially available catheters are: 1) a dual lumen catheter having one lumen (e.g., the blood infusion lumen), that terminates distal to the other lumen (e.g., the blood withdrawal lumen). Some catheters of this type are provided with a midline split (e.g., the Uldall catheter), while others do not have such a split (e.g., the COOK® DDS catheter); 2) a catheter having a slitted valve in the distal tip that acts as a pressure valve opening. This valve opens inwardly for blood aspiration, outwardly for blood infusion, and remains closed when not in use (e.g., the Groshong catheter); 3) various polyester cuffed central venous silicone catheters that are tunneled underneath the skin to reduce infection (e.g., Broviac, Leonard and Hickman catheters); 4) a dual lumen catheter having a tapered tip and two adjacent holes communicating with one lumen just proximal to the tip to assist with outflow, and two adjacent holes communicating with the other lumen (180 degrees removed) just proximal to the first set of holes to assist with inflow (e.g., the Mahurkar catheter); 5) a dual lumen catheter having a diverting structure consisting of a shoulder that has a straight up distal face and a sloped proximal face to reduce access recirculation and raise pressure in the vicinity of the inlet aperture (U.S. Pat. No. 6,409,700); and 6) a catheter designed for femoral approach having two sets of staggered side ports, resulting in a total of four side ports.

One problem with existing hemodialysis catheters is that such catheters can experience decreased flow rates over time. Decreased flow rates may be caused by, among other things, blockage of the withdrawal and/or infusion ports in the catheter. Various factors can cause a port to become blocked. One common cause of port blockage is the inadvertent positioning of one or more ports of the catheter against the vessel wall. This positioning hinders the free flow of fluid through the obstructed port, and in some cases, prevents fluid flow altogether. Another common cause of port blockage is the formation of fibrin sheaths along the ports. Such fibrin sheaths are normally formed in response to the vessel wall washing effect or clotting.

Decreased, or restricted, flow is clearly undesirable in an extracorporeal catheter, such as a hemodialysis catheter. In order for the extracorporeal fluid treatment to be effective, fluid flow through the catheter must not be restricted in any appreciable way. Thus, it is important to position existing catheters in a manner such that fluid flow is not restricted. Additionally, it is important to insure that all ports are unobstructed. Various attempts have been made to reduce port blockage. For example, as described above, some catheters are provided with side ports at various locations on the catheter. Side ports generally provide some reduction in port blockage, however such ports themselves are subject to blockage when placed against the vessel wall, or as a result of fibrin formation on the port. Other attempts have been made to reduce port blockage by providing the stepped side-by-side dual lumen design described above, wherein the respective withdrawal and infusion tubes are of different lengths so that the ports withdraw and infuse the bodily fluid at different axial locations of the catheter. While this arrangement may avoid some problems involved in maintaining adequate flow through the lumens, such catheters can still be subject to suboptimal flow. Some catheters, such as the Mahurkar catheter described above, must be rotated if inflow is blocked because the catheter is up against the vein wall. Although these techniques may be somewhat effective in reducing blockage, reduced flow rate continues to be a problem in the art.

It is desired to provide a multi-lumen catheter for use in the extracorporeal treatment of bodily fluids that minimizes port blockage, and that provides for optimal fluid flow through the lumens of the catheter.

BRIEF SUMMARY

The problems encountered with prior art catheters are addressed by the features of the present invention.

In one embodiment, the present invention comprises a catheter assembly for use in the extracorporeal treatment of bodily fluids. The catheter assembly comprises a catheter body having a withdrawal port, an infusion port, and a plurality of lumens therein. One lumen comprises a withdrawal lumen for transport of fluids withdrawn from a body vessel through the withdrawal port to an extracorporeal treatment unit, such as a dialyzer. Another lumen comprises an infusion lumen for returning fluids treated in the dialyzer to the body vessel via the infusion port. A radially extendable centering wire is provided for centering the catheter assembly in the vessel, to inhibit blockage of the withdrawal and infusion ports. The centering wire extends from an additional lumen in the catheter body to an attachment point on the catheter assembly. Preferably, the centering wire is movable between a first position wherein the wire does not extend radially outwardly, and a second position wherein the wire extends radially outwardly from the catheter body to define a loop.

In another embodiment thereof, the present invention comprises a catheter assembly for use in the extracorporeal treatment of bodily fluids. The catheter comprises a catheter body, wherein the body has first and second cut-out portions along a longitudinal surface thereof. The catheter body has a withdrawal port disposed at the first cut-out portion and an infusion port disposed at the second cut-out portion. The catheter body further has first and second fluid flow lumens therein. The first lumen comprises a withdrawal lumen for receiving fluids from a body vessel through the withdrawal port for transport to an extracorporeal treatment unit, and the second lumen comprises an infusion lumen for receiving treated fluids from the extracorporeal treatment unit for return to the body vessel through the infusion port. One or more centering wires are engaged with the catheter body at the first cut-out portion, and one or more additional centering wires are engaged with the catheter body at the second cut-out portion. Each of the centering wires is capable of extending radially outwardly from the catheter body to form a respective loop for use in centering the catheter assembly in a body vessel.

BRIEF DESCRIPTION OF THE DRAWINGS

FIG. 1 is a side elevational view of a catheter assembly according to one embodiment of the present invention;

FIG. 2 is an enlarged sectional view taken along line 2-2 of FIG. 1;

FIG. 3 is an enlarged sectional view taken along line 3-3 of FIG. 1;

FIG. 4 is an enlarged end view of the catheter body, as viewed from beyond the distal end;

FIG. 5 is a longitudinal view showing the manifold in section, and showing the wire extending beyond the proximal end of the manifold;

FIG. 6 is a fragmented view of the distal end of FIG. 1, shown prior to bowing of the centering wire;

FIG. 7 is an enlarged end view of a catheter body taken from the same orientation as FIG. 4, showing an alternative cross-sectional shape of the fluid flow lumens; and FIG. 8 is an enlarged sectional view of a catheter body as in FIG. 2, illustrating an additional pair of wire lumens;

FIG. 9 is an enlarged sectional view as in FIG. 3, illustrating an additional wire lumen;

FIG. 10 is an enlarged end view of the catheter body as in FIG. 4, illustrating an additional pair of wire lumens;

FIG. 13 is a side elevational view of another embodiment of a catheter assembly;

FIG. 14 is a side view of the embodiment of FIG. 13, rotated 90° from the orientation of FIG. 13, with a portion broken away to illustrate the dual wires;

FIG. 15 is a sectional view of the catheter body taken along line 15-15 of FIG. 13;

FIG. 16 is a longitudinal sectional view of the catheter assembly of FIG. 13

FIG. 17 is an end view of a manifold of the catheter assembly of FIG. 13 as viewed form the proximal end of the assembly, with the wires and extension tubes removed for clarity;

FIG. 18 is an end view of the catheter assembly of FIG. 13; and

FIG. 19 is a side elevational view of the catheter assembly of FIG. 13, showing the wires in a bowed configuration.

DETAILED DESCRIPTION OF THE DRAWINGS AND THE PRESENTLY PREFERRED EMBODIMENTS

Figure 12:
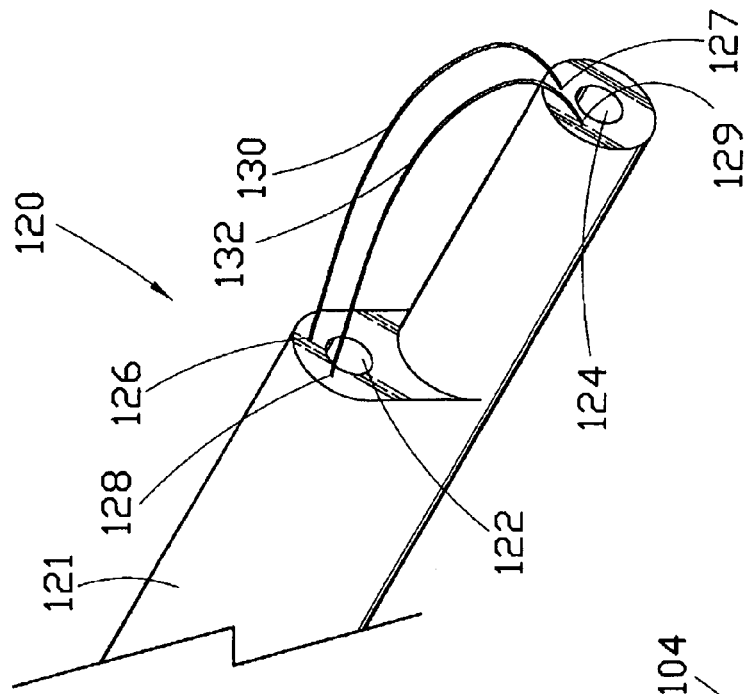
FIG. 12 is a perspective view of another alternative embodiment of a catheter assembly.

For purposes of promoting an understanding of the present invention, reference will now be made to the embodiments illustrated in the drawings, and specific language will be used to describe the same. It is nevertheless to be understood that no limitation of the scope of the invention is thereby intended, the scope of the invention being indicated by the claims appended below and the equivalents thereof. The figures are not all drawn to the same scale to avoid obscuring the details of the finer structures. The following detailed description of the preferred embodiments will make clear the preferred arrangement, size relationships and manner of using the components shown herein.

The present invention is directed to a catheter for use in the extracorporeal treatment of bodily fluids. The bodily fluids are transported from the body through a withdrawal lumen in the catheter, and are thereafter transported to an instrument for extracorporeal treatment. The treated fluids are then returned to the body through an infusion lumen in the catheter. Those skilled in the art will appreciate that the inventive extracorporeal catheter is suitable for multiple uses involving inflow and outflow of bodily fluids. However, the invention will be primarily described hereinafter with reference to one of its intended uses, namely as a hemodialysis catheter for use in the extracorporeal treatment of blood. The hemodialysis catheter enables blood inflow without disturbance, and blood return without hemolysis. In addition to hemodialysis, the catheter can be used for other extracorporeal fluid treatments in which a body fluid is withdrawn from the body, subjected to a treatment process, and thereafter returned to the body. Pheresis and hemofiltration are non-limiting examples of such procedures.

FIG. 1 is a side elevational view of a catheter assembly 10 according to one embodiment of the present invention. In the following discussion, the terms "proximal" and "distal" will be used to describe the axial ends of the apparatus, as well as the axial ends of various component features. The "proximal" end refers to the end of the catheter assembly (or component) that is closest to the operator during use of the assembly. The "distal" end refers to the end of the assembly (or component) that is initially inserted into the patient, or that is closest to the patient. In the orientation of catheter assembly 10 and each of its component features shown in the figures herein, the proximal end is to the left of the page, while the distal end is to the right.

Catheter assembly 10 includes a catheter body 12. Catheter body 12 comprises an outer elongated tubular member formed of a conventional polymer commonly used for such purposes in medical catheters. One example of a preferred polymer for such use is radiopaque polyurethane. Other conventional materials used for such purposes in the medical device art may be substituted. Non-limiting examples of such materials include silicone, nylon and polyethylene. Catheter body 12 has a proximal end 14, a distal end 16 and a plurality of lumens extending therethrough (FIGS. 2 through 4).

In the preferred embodiment shown, catheter assembly 10 includes a bifurcated fitting, such as manifold 20. Manifold may be provided with conventional suture wings 31 if desired. Extension tubes 22, 24 extend in the proximal direction from manifold 20. Extension tubes 22, 24 comprise generally flexible polymers commonly used for such purposes in the medical device art, such as polyurethane, PVC and silicone. Catheter body 12 is received in manifold 20 in conventional fashion, such as by insert molding proximal end 14 in a suitably-sized channel 19 (FIG. 5) in manifold 20. Extension tube 22 communicates, via passageway 21 extending through manifold 20, with fluid withdrawal lumen 40 in catheter body 12 for receiving fluid withdrawn from a body vessel in the patient. A luer lock or other suitable connector 26 is fitted onto the proximal end of extension tube 22 in conventional fashion. During use of catheter assembly 10, connector 26 engages in mating relationship with a connector associated with an ingress opening of a treatment instrument 50, such as a dialyzer, for establishing a flow path of blood to the dialyzer. Extension tube 24 communicates, via passageway 23 extending through manifold 20, with blood infusion lumen 42 in catheter body 12. A luer lock or other suitable connector 28 is fitted onto the proximal end of extension tube 24. During use of catheter assembly 10, connector 28 engages in mating relationship with a connector associated with an egress opening of dialyzer 50 for receiving treated blood from the dialyzer. Dialyzer 50 and its ingress and egress openings are shown schematically in FIG. 1. Conventional clamps 27, 29 may be provided for selectively controlling the flow of blood between the dialyzer and the catheter body.

Catheter body 12 may be further understood upon viewing FIGS. 2 through 4. FIG. 2 is an enlarged sectional view taken along line 2-2 of FIG. 1. FIG. 3 is an enlarged sectional view taken along line 3-3 of FIG. 1. FIG. 4 is an enlarged end view of the catheter body, as viewed from beyond the distal end. These figures illustrate the presence and the relative orientation of lumens 40, 42, 44, 46 that extend through catheter body 12. Wire 52 has been omitted from FIGS. 2-4 to permit clear visualization of the lumens. Fluid withdrawal lumen 40 extends from withdrawal port 41 to the proximal end of catheter body 12. Fluid infusion lumen 42 extends from infusion port 43 to the proximal end of catheter body 12. In the preferred embodiment shown, withdrawal lumen 40 terminates proximal to infusion lumen 42. This arrangement is preferred, but not crucial to the invention. Alternatively, the return lumen can terminate proximal to the withdrawal lumen, or the lumens can have the same length.

FIG. 1 also illustrates the presence of centering wire 52. In this embodiment, centering wire 52 extends externally of catheter body 12 from wire lumen 44 to wire lumen 46, in a manner to be described. The exposed portion of wire 52 shown in FIG. 1 bows outwardly in the radial direction as shown. By bowing outwardly in this manner, centering wire 52 acts to increase the effective outer diameter of catheter body 12. As a result, the withdrawal and infusion ports 41, 43 are spaced from the vessel wall, thereby freeing the ports from obstruction and maintaining the free flow of fluid through the catheter.

Smaller diameter lumens 44, 46 serve as conduits for centering wire 52. In a preferred embodiment, centering wire 52 extends from manifold 20 in the distal direction through wire lumen 44. Preferably, the proximal end of wire 52 extends proximally beyond manifold 20 through wire channel 25, as shown in FIG. 5. A cap or similar stop mechanism 54 (shown schematically in FIG. 5) is engaged with the proximal end of wire 52. Stop mechanism 54 limits the amount of wire 52 that can pass through manifold wire channel 25, thereby limiting the amount of wire available to bow exteriorly of assembly 10, as shown in FIG. 1. Alternatively, a pusher mechanism such as mechanism 176 (FIG. 14) may be utilized. Manifold channel 25 is optional, and the catheter assembly can be formed such that the proximal end of wire 52 extends through either of manifold passageways 21 or 23. Alternatively, the catheter assembly can be constructed such that the proximal end of wire 52 protrudes from any other convenient site on the assembly.

When the wire is aligned in the position shown in FIG. 5 with the proximal end of the wire protruding a fixed distance in the proximal direction beyond manifold 20, the distal end of wire 52 is not bowed, but rather, lays substantially flat in the axial portion of catheter body 12 between lumens 44 and 46, as shown in FIG. 6. As cap 54 is advanced from the position shown in FIG. 5 toward manifold 20, the distal end of wire 52 protrudes further in the distal direction through lumen 44, and the springiness of wire 52 causes it to bow outwardly, as shown in FIG. 1. Those skilled in the art will appreciate that the length of the wire can be varied, and the proximal extension of the wire beyond manifold 20 can also be varied, according to the amount of bowing desired and the diameter of the vessel into which the catheter is to be inserted.

In the embodiment shown, the distal end of wire 52 is received in wire lumen 46. Preferably, the distal end of wire 52 is securely adhered to a convenient site in the interior of lumen 46 by any conventional means, such as adhesion. If desired, a dedicated channel, groove, or like structure can be provided in lumen 46 to receive the distal end of wire 52. Only a short length of wire 52 need extend into lumen 46, such as 2 to 3 mm. Those skilled in the art will appreciate that since the wire is only adhered to the distal end of lumen 46 in this embodiment, that lumen 46 need not extend longitudinally throughout catheter body 12. However, for production purposes, it is generally more convenient to form all of the lumens so that they extend all the way through catheter 12. Although it is preferred that distal end of wire 52 be adhered to the interior of lumen 46, this need not be the case. Rather, the distal end of the wire can be adhered or otherwise secured to other convenient sites of the catheter assembly. Alternatively, the wire can be formed such that its distal end extends all the way back through lumen 46 to a convenient proximal attachment position, such as at manifold 20.

Those skilled in the art will appreciate that there are numerous other ways in which the wire can be attached to the catheter assembly in order to result in a structure in which the wire bows outwardly as shown in FIG. 1, such alternatives being within the scope of the invention. For example, rather than extending one end of wire 52 fully through lumen 44 such that its proximal end extends proximally through manifold channel 25 as described, a catheter assembly having a bowed portion as shown in FIG. 1 can be formed by simply securing a small wire fragment to the catheter assembly in a manner such that the wire fragment extends radially outwardly from catheter body 12 in the manner shown in FIG. 1. One preferred way of doing this is to provide attachment points in the interior of each of lumens 44, 46, and to insert the respective ends of the wire fragment a few millimeters into each of lumens. The respective ends can then be secured to the catheter body 12 at a convenient attachment point in each of the lumens. Similarly, a wire 52, or smaller wire fragment as described, can be attached to other convenient attachment points on the catheter assembly, in which event wire channel 25, stop mechanism 54, and/or even lumens 44, 46 may be unnecessary.

As will be appreciated by those skilled in the art, the particular mechanism for attaching the wire to the catheter assembly is not critical to this invention, nor is the length of wire employed. Similarly, it is not critical that the wire extend from the distal end of the catheter assembly. Rather, all such attachment mechanisms, point of attachment along the catheter body, and wire lengths are considered within the scope of the invention, as long as a desired function of maintaining a spacing between the respective withdrawal and infusion ports 41, 43, and the wall of the vessel, can be achieved thereby.

Centering wire 52 is preferably formed of a metal, such as nitinol or coiled stainless steel. Those skilled in the art will recognize that wire formed from other compatible materials, including other metals, non-metals, monofilaments, polymers and various composite materials may be substituted. Preferably, the material used to form wire 52 should be flexible or resilient. In this manner, the wire bows to the position shown in FIG. 1 once it is passed through lumen 44, and is capable of maintaining a substantially bowed configuration upon contact with a vessel wall.

As shown in the embodiment of FIGS. 2 through 4, the diameter of the fluid flow lumens, namely lumens 40, 42, is generally much greater than the diameter of the wire lumens, namely lumens 44, 46. Since lumens 40, 42 carry the bodily fluid therethrough, it is desirable that such lumens have as large a diameter as possible so that the largest volume of fluid can be transported. Lumens 44, 46, on the other hand, need only have a diameter large enough to accommodate wire 52. The diameter of the fluid flow lumens will generally be about 2-4 times, preferably about 3 times, the diameter of the wire lumens.

FIG. 7 is an end view of catheter body 12 as in FIG. 4. The embodiment shown in FIG. 7 is otherwise similar to that shown in FIG. 4, except that in this embodiment the fluid flow lumens 60, 62 have a D-shaped, semi-circular cross section, rather than the circular cross-section shown in FIG. 4. The D-shaped cross section may provide more cross-sectional flow area, and thereby improve fluid flow. Other cross-sectional shapes may also be substituted. It is known in the medical arts to utilize catheter lumens of various cross-sectional configurations, and all such variations are considered within the scope of the invention.

Although the embodiments described previously include a catheter body 12 and a single centering wire, the invention is not so limited. Rather, multiple centering wires can be provided. For example, rather than utilizing a single centering wire 52, as in the embodiment of FIGS. 1-7, two or more centering wires may be provided, as shown in the catheter body 80 of FIGS. 8-10. Catheter body 80 includes withdrawal lumen 90 and infusion lumen 92 as in the previously-described embodiment, and includes an additional set of wire lumens to accommodate two centering wires, rather than a single wire. Thus instead of the single set of wire lumens 44, 46 as shown in FIGS. 2-4 that accommodate centering wire 52, FIGS. 8-10 include two sets of wire lumens 82, 84 and 86, 88, respectively. A first centering wire (not shown) can therefore extend between lumens 82 and 84, and a second centering wire (not shown) can extend between lumens 86 and 88 in the same manner as in the previous embodiment. Lumens 82, 84 and 86, 88 can extend all the way through catheter body 80, or terminate at a lesser distance. Similarly, the manifold can be appropriately modified to provide an additional passageway for the second wire, if desired.

Figure 11:
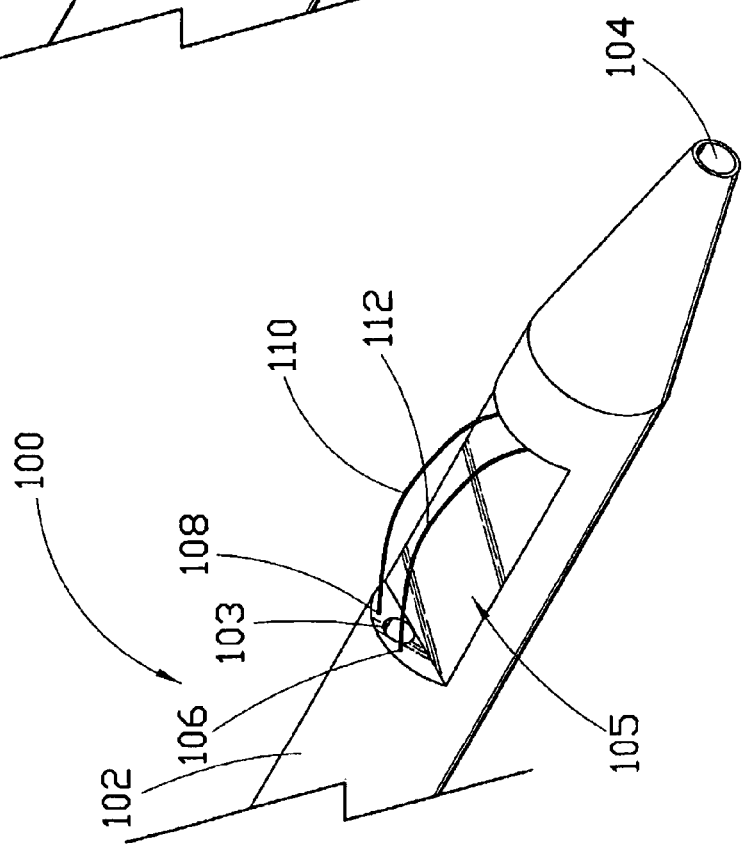
FIG. 11 is a perspective view of an alternative embodiment of a catheter assembly.

FIGS. 11 and 12 illustrate additional embodiments of catheter assemblies 100, 120 that include one or more centering wires. In FIG. 11, catheter assembly 100 includes two generally parallel wires 110, 112 that bow outwardly from the catheter body 102. In this embodiment, a segment of the catheter body 102 is removed, thereby forming a channel 105. Withdrawal port 103 is disposed in channel 105, and infusion port 104 is provided at the distal end of catheter body 102. Fluid flow lumens (not shown) extend in the proximal direction from respective withdrawal and infusion ports 103, 104, as described in the previous embodiments. In this embodiment, wire 110 extends between wire lumen 108 and a corresponding lumen or other attachment point (not shown) on the opposite side of the channel, and wire 112 extends between wire lumen 106 and a corresponding lumens or other attachment point (not shown) on the opposite side of the channel.

The embodiment of a catheter assembly 120 of FIG. 12 is similar in many respects to the embodiment of FIG. 1. Catheter assembly 120 includes withdrawal port 122 and infusion port 124 in catheter body 121 as shown, and includes two centering wires 130, 132. Wire 130 extends from lumen 126 to lumen 127 as shown. Wire 132 extends from lumen 128 to lumen 129 as shown. The catheter assemblies shown in respective FIGS. 11 and 12 can be structured such that the dual centering wires can be selectively bowed by manipulating an extended portion of the centering wire in the manner of the previously-described embodiments, or alternatively, can be formed to have a permanently-bowed configuration.

Another embodiment of a catheter assembly 140 is shown in FIGS. 13-19. In this embodiment, catheter assembly 140 comprises a catheter body 142 and a manifold 144 engaged with the proximal end of catheter body 142. Manifold 144 may be provided with conventional suture wings 146. Extension tubes 148, 150 extend in the proximal direction from manifold 142, and luer locks 152, 154 may be provided at the proximal ends of extension tubes 148, 150.

Catheter body 142 is provided with respective cut-out portions 156, 158. Cut-out portions 156, 158 preferably have a semi-circular configuration, but may alternatively have other configurations, such as the channel configuration of FIG. 11. Catheter body 142 is provided with multiple lumens, as shown in the cross-sectional view of FIG. 15. Large lumen 160 comprises the withdrawal lumen and large lumen 162 comprises the infusion lumen. Smaller diameter lumens 163-166 comprise wire lumens. Preferably, as shown in FIG. 16, a wire guide lumen 161 extends from one of the lumens, such as infusion lumen 162 in the embodiment shown, to the distal end of the catheter body 142, to enable passage therethrough of a wire guide.

As shown in FIG. 17, a manifold 142 may be provided with large passageways 168, 170, and smaller passageways 171-174. Although smaller passageways 171-174 are not required, when present these passageways permit passage therethrough of the proximal ends of respective wires 177-180. When the device is assembled as shown in FIG. 13, manifold passageway 168 communicates with one of the large lumens 160, 162 from the catheter body, and manifold passageways 170 communicates with the other large lumen from the catheter body. Each of manifold smaller passageways 171-174 communicates with a separate one of catheter body small lumens 163-166. Those skilled in the art will appreciate that it is not necessary that four small passageways 171-174 be provided in all instances, and that some of these passageways, such as for example passageways 171 and 172, and passageways 173 and 174, may be consolidated into a single passageway.

As shown in FIG. 18, a pusher mechanism, such as generally U-shaped end piece 176, is provided at the proximal end of the catheter assembly. In the embodiment shown, a pair of centering wires, namely wires 177, 178 and 179, 180, respectively, span respective cut-out portions 156, 158. Centering wires 177-180 extend in the distal direction from end piece 176. When the device is fully assembled, each wire 177-180 preferably extends through a separate one of manifold lumens 171-174 and mating catheter body lumen 163-166. Wires 177-180 can be attached to the distal portion of catheter body 142 by any of the mechanisms described above, or through one or more additional lumens (not shown).

During operation, pusher mechanism 176 is initially withdrawn in the proximal direction as shown in FIGS. 13 and 14. As the pusher mechanism is advanced in the distal direction, each of wires 177-180 is advanced distally through its respective manifold lumen 171-174 and catheter body lumen 163-166. When the pusher mechanism approaches the proximal end of manifold 144, exposed portions of the respective wires are bowed outwardly, as shown in FIG. 19. Pusher mechanism 176 can be provided with a snap-fit connector 182 that is received in mating orifice 145 in manifold 144 to secure the pusher mechanism to manifold 144, and thereby maintain the bowed configuration.

Although the embodiments of FIGS. 11-19 illustrate a catheter assembly having two centering wires, those skilled in the art will appreciate that with minor modifications to the catheter body and/or the manifold, the assembly can be adapted to accommodate more, or fewer, centering wires. Those skilled in the art will appreciate that in the event that other than two centering wires are utilized, the catheter body may be modified to provide an appropriate number of lumens and/or attachments points to account for the number of wires utilized. Such modification is believed routine in view of the teachings provided herein.

Although the figures provided herein illustrate single body catheters such as the COOK DDS catheters, available from Cook Critical Care, of Bloomington, Ind., those skilled in the art will recognize that the invention is equally applicable with only minor modification to use with other conventional catheters, such as split-body catheters.

It is therefore intended that the foregoing detailed description be regarded as illustrative rather than limiting, and that it be understood that it is the following claims, including all equivalents, that are intended to define the spirit and scope of this invention.

The invention claimed is:

1. A catheter assembly for use in the extracorporeal treatment of bodily fluids, comprising:
   a catheter body, said catheter body having a withdrawal port, an infusion port, and a plurality of lumens therein; one of said lumens comprising a withdrawal lumen for transport of fluids withdrawn from a body vessel through said withdrawal port to an extracorporeal treatment unit, and another of said lumens comprising an infusion lumen for infusion of treated fluids from said extracorporeal treatment unit through said infusion port into the vessel, said catheter body including at least one additional lumen; and a wire extending from said at least one additional lumen to an attachment point on said catheter assembly, said wire defining a loop extending radially outwardly from said catheter body and oriented in a manner such that when said catheter is in said vessel said wire maintains a spacing between said withdrawal port and a wall of said vessel;
   said catheter assembly further comprising a manifold disposed at a proximal end of said catheter body, wherein a proximal end of said wire extends through said at least one additional lumen and said manifold and a distal end of said wire comprises said radially extending portion; the proximal end of said wire being movable between a first position wherein said wire distal end does not extend radially outwardly, and a second position wherein said wire distal end extends radially outwardly from said catheter body to define said loop; and
   a stop member at said proximal end of said wire for selectively limiting movement of said wire between said first and second positions to a defined distance.

2. A catheter assembly, for use in the extracorporeal treatment of bodily fluids, comprising:
   a catheter body, said catheter body having a withdrawal port, an infusion port, and a plurality of lumens therein; one of said lumens comprising a withdrawal lumen for transport of fluids withdrawn from a body vessel through said withdrawal port to an extracorporeal treatment unit, and another of said lumens comprising an infusion lumen for infusion of treated fluids from said extracorporeal treatment unit through said infusion port into the vessel, said catheter body including at least one additional lumen; and a wire extending from said at least one additional lumen to an attachment point on said catheter assembly, said wire defining a loop extending radially outwardly from said catheter body and oriented in a manner such that when said catheter is in said vessel said wire maintains a spacing between said withdrawal port and a wall of said vessel;
   wherein said catheter body includes a channel portion, said withdrawal port being disposed at said channel portion; wherein said channel portion has a proximal end and a distal end, and wherein said wire spans said channel portion from said proximal end to an attachment point at said distal end.

3. The catheter assembly of claim 2, wherein said at least one additional lumen comprises two lumens, said two lumens communicating with said channel portion, wherein a separate wire extends from each of said two lumens to a respective attachment point at a distal end of said channel portion.

4. The catheter assembly of claim 3, said catheter assembly further comprising a manifold disposed at a proximal end of said catheter body, wherein a proximal end of each of said wires extends through said additional lumens and through said manifold.

5. The catheter assembly of claim 4, said assembly further comprising a pusher mechanism proximal to said manifold, wherein the respective proximal ends of each of said wires engage said pusher mechanism, said pusher mechanism selectively movable between a first position wherein said wires do not define a loop and a second position wherein said wires define said radially outwardly extending loop.

6. A catheter assembly for use in the extracorporeal treatment of bodily fluids, comprising:
   a catheter body, said catheter body including first and second cut-out portions along a longitudinal surface thereof, said catheter body having a withdrawal port disposed at said first cut-out portion and an infusion port disposed at said second cut\-out portion, said catheter body further having first and second fluid flow lumens therein, said first lumen comprising a withdrawal lumen for receiving fluids from a body vessel through said withdrawal port for transport to an extracorporeal treatment unit, and said second lumen comprising an infusion lumen for receiving treated fluids from said extracorporeal treatment unit for return to said body vessel through said infusion port; and
   a centering wire engaged with said catheter body at said first cut-out portion, and another centering wire engaged with said catheter body at said second cut-out portion, each of said centering wires capable of extending radially outwardly from said catheter body to form a respective loop.

7. The catheter assembly of claim 6, wherein said infusion port is positioned distal to said withdrawal port along said catheter body.

8. The catheter assembly of claim 7, wherein said centering wire at said first cut-out portion comprises a first centering wire, said catheter assembly further comprising a second centering wire disposed substantially parallel to said first centering wire at said first cut-out portion; and wherein said centering wire at said second cut-out portion comprises a third centering wire, said catheter assembly further comprising a fourth centering wire disposed substantially parallel to said third centering wire at said second cut-out portion.

9. The catheter assembly of claim 8, said catheter assembly further comprising a manifold disposed at a proximal end of said catheter body, said manifold including at least two passageways therethrough, a first one of said passageways communicating with said withdrawal lumen and a second one of said passageways communicating with said infusion lumen; a first extension tube engaged with a proximal end of said first passageway for receiving said withdrawn fluid for transport to said treatment unit, and a second extension tube engaged with a proximal end of said second passageway for receiving treated fluid from said treatment unit for transport to said infusion lumen.

10. The catheter assembly of claim 9, wherein said catheter body includes a plurality of wire lumens therein, a first wire lumen extending from said first cut-out portion to the proximal end of said catheter body, and a second wire lumen extending from said second cut-out portion to said proximal end of said catheter body, at least one of said first and second wires received in said first wire lumen and at least one of said third and fourth wires received in said second wire lumen.

11. The catheter assembly of claim 10, wherein said manifold comprises at least a third passageway, and wherein the proximal end of at least one of said centering wires extends proximally through said third passageway.

12. The catheter assembly of claim 10, wherein said manifold further comprises at least third and fourth passageways, and wherein at least one of said centering wires extends proximally through each of said third and fourth passageways.

13. The catheter assembly of claim 12, said assembly further comprising a pusher mechanism proximal to said manifold, wherein the respective proximal ends of each of said wires engage said pusher mechanism, said pusher mechanism movable between a first position wherein said wires do not define a loop and a second position wherein said wires define said radially outwardly extending loop.

14. The catheter assembly of claim 9, said catheter body including two wire lumens extending from said first cut-out portion to the proximal end of said catheter body, said first wire received in one of said lumens and said second wire received in the other of said lumens; said catheter body further including two additional wire lumens extending from said second cut-out portion to said proximal end of said catheter body, said third wire received in one of said additional lumens and said fourth wire received in the other of said additional wire lumens.

15. The catheter assembly of claim 14, wherein said manifold includes a separate passageway therethrough for each of said wires, and wherein a proximal end of each said wire extends proximally through each of said passageways.

16. The catheter assembly of claim 15, said assembly further comprising a pusher mechanism proximal to said manifold, wherein the respective proximal ends of each of said wires engage said pusher mechanism, said pusher mechanism movable between a first position wherein said wires do not define a loop and a second position wherein said wires define said radially outwardly extending loop.

\* \* \* \* \*